United States Patent [19]

Zentman

[11] 4,040,416
[45] Aug. 9, 1977

[54] ORTHOPEDIC SPLINT

[76] Inventor: Leo Zentman, c/o Orthopedic Splints, Inc. 147 Albany Ave., Lindenhurst, N.Y. 11757

[21] Appl. No.: 708,043

[22] Filed: July 23, 1976

[51] Int. Cl.² ............................................. A61F 3/00
[52] U.S. Cl. ................................................... 128/80 A
[58] Field of Search ............... 128/80 R, 80 A, 80 C, 128/80 B, 83, 87 R, 584

[56] References Cited

U.S. PATENT DOCUMENTS 3,477,426  11/1969  Wincheski .................... 128/80 R
3,777,747  12/1973  Friedman ..................... 128/80 A

OTHER PUBLICATIONS

"The Duo-Plex Night Splint" Herbst Shoe Mfg. Co. Catalogue, Received May 1966.

Primary Examiner—John D. Yasko
Attorney, Agent, or Firm—Bauer, Amer & King

[57] ABSTRACT

A spreader bar type orthopedic splint, i.e. with a bar which holds the patient's feet spread apart and at a corrective toed in or toed out angle, in which the bar or feet-spreading member is a flexible, planar body, preferably fabricated of a leaf spring metal, so that the patient can partake of limited exercising movements as permitted by the flexuring of the body out of its plane. It is significant that excluded from the permitted exercising movements is any movement that is rotative about the reference axis used to set the corrective angle of the patient's feet, since such movements would require bending or flexing of the flat body in its own plane, a degree of movement that the body strongly resists despite its flexibility. By excluding this degree of movement, the therapeutic value of the splint is preserved since there is a corresponding preservation of the corrective angle, despite exercising movements of the patient.

1 Claim, 6 Drawing Figures

U.S. Patent     Aug. 9, 1977     4,040,416
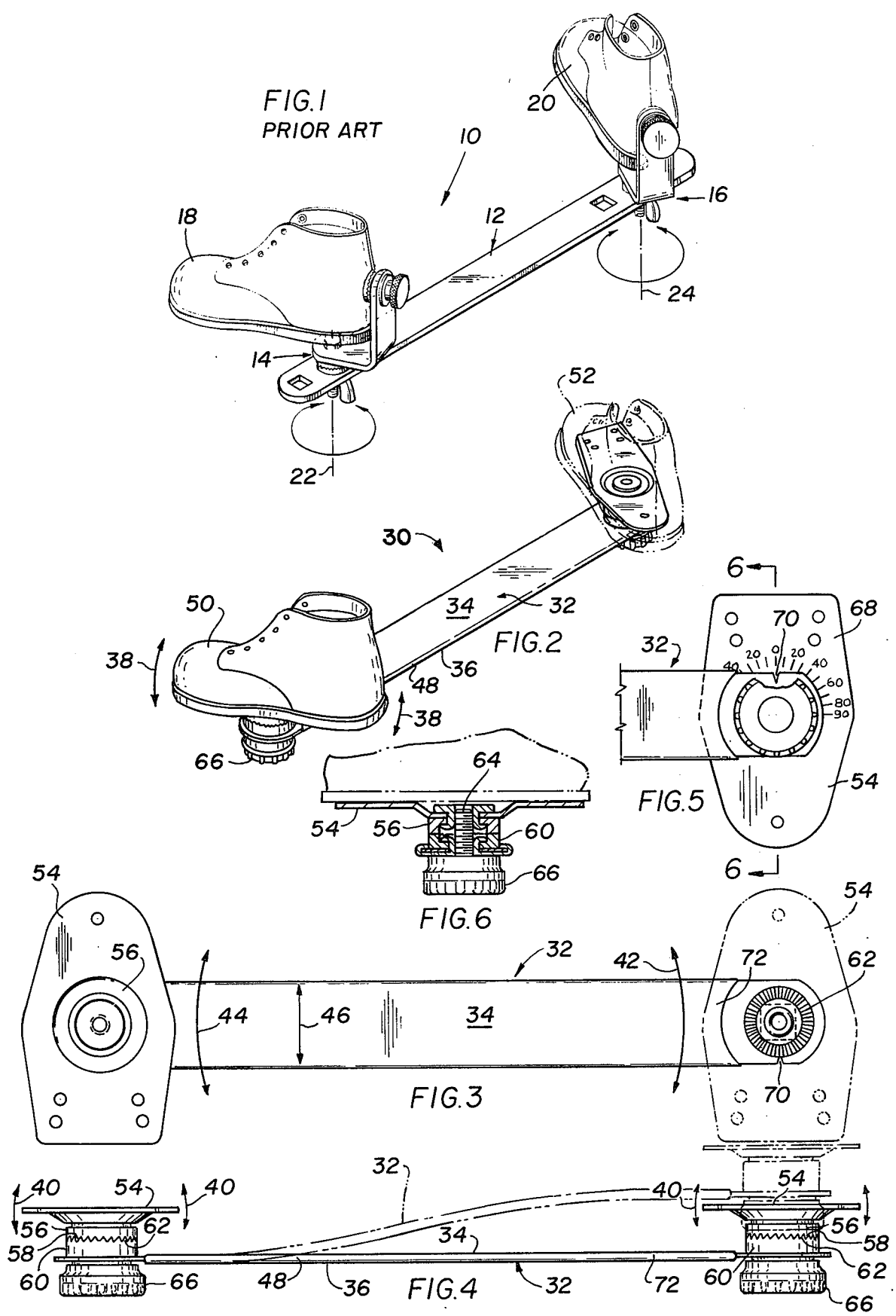

ORTHOPEDIC SPLINT

The present invention relates generally to orthopedic splints, and more particularly to an improved splint which effectively holds the patient's feet in a corrective angular orientation and, while doing so, allows limited movements for exercising purposes in directions which do not undermine the therapeutic value of the splint.

As generally understood, an orthopedic splint is useful in correcting bone deformities, particularly in infants, by holding the patient's feet at an appropriate corrective angle. Thus, if the patient's feet are abnormally toed-in, during and for a specified period, it is recommended that the patient wear the splint which holds his feet in a corrective toed-out angle or orientation. This use of the splint, unfortunately, is uncomfortable to most children, and despite considerable effort to alleviate this discomfort, there are no known orthopedic splints which are entirely satisfactory.

Broadly, it is an object of the present inventin to provide an improved orthopedic splint overcoming the foregoing and other shortcomings of the prior art. Specifically, it is an object to lessen the discomfort of the orthopedic splint by allowing limited exercising movements during its use, but excluding any exercising movement in a direction which counteracts the therapeutic purpose of the splint.

In the classification or types of orthopedic splints which have a spreader bar with rotatably adjustable shoe-engaging plates at opposite ends thereof, an improved splint which demonstrates objects and advantages of the present invention includes the use for said spreader bar of a flexible construction material, such as leaf spring steel, in an elongated rectangular planar body which extends in spanning relation between the shoe-engaging plates. This construction material and shape allows limited movement in the user's feet only in rocking movements relative to each rotation axis of the shoe-engaging plate, said rocking movements being permitted by the flexuring of the body out of its plane. It is also significant that any attempt to partake of a rotative movement about either said rotation axis is effectively resisted by the inability of the body to flex within its plane. In this way, the user or patient can partake of exercise movements during use of the orthopedic splint without undermining the therapeutic value thereof.

The above brief description, as well as further objects, features and advantages of the present invention, will be more fully appreciated by reference to the following detailed description of a presently preferred, but nonetheless illustrative embodiment in accordance with the present inventon, when taken in conjunction with the accompanying drawings, wherein:

FIG. 1 is a perspective view of a typical prior art orthopedic splint;

FIGS. 2—6 illustrate the improved orthopedic splint according to the present invention. More particularly, FIG. 2 is a perspective view of such splint in which a twisting degree of movement in the spreader bar is illustrated by the full line and phantom line perspective of this structural component. Also, one shoe attached to an end of the spreader bar is illustrated in phantom line perspective to more clearly illustrate the shoe-attaching structure of the splint;

FIG. 3 is a plan view of the improved orthopedic splint which most clearly illustrates the flat plane or body which comprises the spreader bar;

FIG. 4 is an end elevational view projected from FIG. 3, showing further structural details, and also illustrating in phantom line perspective how the spreader bar can be bowed or flexed out of its plane;

FIG. 5 is a partial plan view of one end of the slint which illustrates the indexing structure which is utilized to set the angular orientation of the shoes; and FIG. 6 is a side elevational view, in section, taken along lines 6—6 of FIG. 5, illustrating further structural details.

FIG. 1 illustrates a typical prior art orthopedic splint, generally designated 10. The within inventive splint, illustrated in FIGS. 2-6, is an improvement of this type of splint. In this connnection, splint 10 is of the type or class which includes a rigid, inflexible spreader bar 12 which at opposite ends has shoe-engaging mechanisms 14 and 16. From a therapeutic point of view, and as is generally understood, the function of the spreader bar 12, as its name implies, is to hold the patient's feet which are placed in each of the shoes 18 and 20 in a spread apart position. Each shoe-engaging means 14 and 16 is rotatable about a rotation axis, as exemplified by the axis 22 associated with the shoe-engaging means 14. Thus by making an appropriate adjustment relative to each rotation axis, the shoes 18 and 20 can either be set in an outwardly diverging fashion, as illustrated in FIG. 1, or they can be placed in an inwardly diverging orientation, depending upon what orientation counteracts the bone disfiguration that exists in the patient.

In summary, a typical prior art orthopedic splint, as exemlified by the splint 10, thus effectively holds the patient's legs in a predetermined angular orientation, either pointing out or pointing in, and, more important for our present purposes, does not allow any exercising movements. Undoubtedly the patient's legs are held rigidly in place as just explained because to allow these exercise movements would possibly allow rotative movement in the patient's legs which would counteract the corrective angular orientation, and thus these exercise movements might undermine the therapeutic value of the orthopedic splint 10.

As will now be explained in connection with FIGS. 2-6, the within improved orthopedic splint of the present invention readily allows for exercise movements, and, in doing so, restricts these exercising movements to movements or traverses which are other than rotative about the rotaton axis of either of the shoe-engaging means. In other words, the patient or user of the improved orthopedic splint hereof can make limited directional movements while wearing the splint hereof, these movements being in all directions except those which counteract the corrective angular orientation. As a result, the patient can exercise his legs and in doing so will not undermine the therapeutic value of the orthopedic splint.

The above just described significant functioning of the orthopedic splint hereof is perhaps best understood from a consideration of FIGS. 2 and 4. As illustrated in these figures, the improved splint, generally designated 30, includes, as does the noted prior art splint, a spreader bar or element 32. However, in the case of the improved splint 30, the spreader element 32 is fabricated of a flexible construction material, which in a preferred embodiment consists of tempered or case hardened steel of the type normally known as "shim" metal used in leaf springs or for the manufacture of hacksaw blades. This material is known for its hardness and also for its flexibility. Not only is the spreader bar 32 fabricated of a flexible construction material, but as clearly illustrated it is formed as an elongated flat rectangular body with flat top and lower surfaces 34 and 36, respectively. The flexible spreader bar 32 therefore can be characterized as a planar body. An important contribution of the present invention is the recognition that a planar body, as exemplified by the spreader bar 32, can be readily flexed, but only out of its plane; or, stated another way, that a planar body cannot be flexed within its plane. This will now be explained in conjunction with FIGS. 2, 4 and also FIG. 3.

As illustrated in FIG. 2, any rocking movement 38 by either one or both of the patient's feet will readily be permitted by the flexible spreading bar 32. This subjects this structural element to a twisting movement, which is a degree of movement it can readily partake of. This is illustrated in FIG. 2 by the phantom line perspective of the spreader bar 32.

Referring to FIG. 4, similarly any rocking movement 40 by either or both of the patient's feet would be permitted by an appropriate direction of bowing in the flexible spreader bar 32. This also is illustrated by the phantom line perspective of this structural element.

Referring now to FIG. 3, any exertion of a force by the patient which tends to, or attempts to, bent or flex the spreader bar 32 in the direction designated by the double headed arrow 44 is effectively resisted by the spreader bar 32, despite its flexibility. The reason for this is that the direction 44 is in the plane of the spreader bar which, of course, coincides with the width 46 of the top and bottom surfaces 34, 36. As will be generally appreciated, the width 46 is of course too extensive to yield to any force exerted in the direction 44; whereas on the other hand, the comparatively smaller sized thickness 48 of the rectangular body (see FIGS. 2, 4) will of course yield to forces generated by the previously noted rocking movements 38 and 40. In this manner, the rectangular spreader bar 32, although flexible, is selective in the degree of movement which it permits in the patient's feet. In summary, it will permit rocking movements 38 and 40 by appropriately flexing, as shown in phantom perspective in FIGS. 2 and 4, out of its plane, but it will not permit any rotative movements, as in the direction 44, relative to each rotation axis of the shoe-engaging means of the splint. This latter movement, of course, should not be permitted since this direction of movement would counteract the corrective angular orientation in which each foot of the patient is being held by the splint.

For completeness sake, and also to describe a fully working embodiment, note is made of the following additional structural features of the splint 30 hereof. These additional features include left and right shoes 50, 52, respectively, each appropriately affixed to a plate 54. As is perhaps best illustrated in FIG. 6, mounted centrally of a depression in each plate 54 and connected to extend in depending relation therefrom is a first nut member 56 with circumferentially spaced radial serations 58 (see FIG. 3). Cooperating with nut 56 is a second nut 60 with intermeshing circumferentially spaced serations 62. Nut 60 is fixedly mounted adjacent each opposite end of the spreader bar 32 and has a central bore through which the threaded shank 64 of a connector 66 is projected. The threaded shank 64 threadably engages with the threaded upper portion of the nut 56.

Thus connector 66 is effective in connecting the nuts 60 and 56 together in facing relation. In this manner, it is possible to locate nut 56 in any angular orientation in relation to the nut 60, and then connect these two nuts together in this angular orientation. Naturally, the intermeshing serations 58 and 62 of these nuts facilitate in holding the nuts in the selected angular orientation.

To assist in selecting an apropriate corrective angle for the patient there is provided on the bottom surface of each shoe plate 54 a circumferential arrangement 68 of angle notations. The arrangement 68 is correlated with an indexing notch provided in a strategic location at the end of the spreader bar 32. As illustrated in FIG. 5, the angular orientation of shoe plate 54 relative to the spreader bar 32 is "0" since a 90° angle exists between these two components. However, it should be readily apparent that by rotating the shoe plate 54 so that notch 70 aligns with one of the angle indications in the arrangement 68 that a rotative position can be readily selected for the shoe plate 54.

Since the improved splint 30 hereof is intended to be used for children, as a precaution the actual spreader bar body 32 is placed within a protective plastic sleeve 72 and thus minimizes any possibility of the child being cut, scratched or otherwise harmed by this structural member. In order of assembly, one of the two plates 54 is assembled at one end of the spreader bar 32, sleeve 72 is then placed upon the spreader bar 32, and then the other shoe plate 54 assembled to the remaining end of the spreader bar.

From the foregoing description, and particularly that related to the flexuring of the spreader bar 32 out of its plane, as described particularly in connection with FIGS. 2 and 4, it should be readily appreciated that the orthopedic splint 30 hereof readily permits exercising movements, but not at the expense of lessening the therapeutic value of the splint. More particularly, the exercising movements are restricted only to rocking movements 38 and 40 relative to the rotation axis of each plate 54, and specifically excludes any movement in the child's foot that could be considered a rotative movement about the rotation axis of either of the shoe plates 54. Exclusion of this movement thus maintains the effectiveness of the orthopedic splint.

A latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein.

What is claimed is:

1. In an improved orthopedic splint comprising a pair of shoe-engaging plates for attachment to the shoes of a patient using said splint, spaced apart rotation axis-defining means for rotatably mounting each said shoe-engaging plate preparatory to urging each said shoe-engaging plate through a rotatable traverse about one said cooperating rotation axis incident to fixing said shoe-engaging plates in a selected angular relation to each other, and a flat, normally horizontally disposed planar connecting member of metallic leaf spring construction material flexible up and down from said horizontal plane and connected in spanning relation between said spaced apart rotation axis-defining means for allowing limited movement of said shoe-engaging plates and the patient's feet only in rocking movement relative to each other up and down from the horizontal plane as limited by the planar member, said rocking movement being permitted by the flexuring of said member up and down out of its normally horizontal plane while preventing any rotative movement about either of said rotation axes of said shoe-engaging plates to retain said plates and the patient's feet in their fixed selected angular relationship to each other so that the patient can partake of exercise movements in the up and down directions, but not rotatively during use of said orthopedic splint.

* * * * *